United States Patent [19]

Ramsay et al.

[11] Patent Number: 5,192,777
[45] Date of Patent: Mar. 9, 1993

[54] MACROLIDE COMPOUNDS

[75] Inventors: Michael V. J. Ramsay, South Harrow; Edward P. Tiley, Pinner; Derek R. Sutherland, Chalfont St Giles, all of United Kingdom

[73] Assignee: American Cyanamid Company, Stamford, Conn.

[21] Appl. No.: 626,125

[22] Filed: Dec. 11, 1990

Related U.S. Application Data

[63] Continuation of Ser. No. 242,184, Sep. 9, 1988, abandoned.

[30] Foreign Application Priority Data

Sep. 11, 1987 [GB] United Kingdom ................ 8721377

[51] Int. Cl.$^5$ .................. A61K 31/44; A61K 31/38; A61K 31/335; C07D 315/00
[52] U.S. Cl. ................. 514/333; 514/336; 514/422; 514/444; 514/450; 514/63; 546/269; 546/14; 548/518; 548/525; 548/527; 548/406; 549/60; 549/264; 549/214
[58] Field of Search ............. 549/264; 514/450, 422, 514/333; 546/269; 548/518

[56] References Cited

U.S. PATENT DOCUMENTS 4,579,864 4/1986 Linn et al. ........................ 514/450

FOREIGN PATENT DOCUMENTS 0110667 6/1984 European Pat. Off. .
0259779 3/1988 European Pat. Off. .

Primary Examiner—Alan L. Rotman
Assistant Examiner—Amelia A. Owens
Attorney, Agent, or Firm—Peggy A. Climenson

[57] ABSTRACT

Compounds of formula (I)

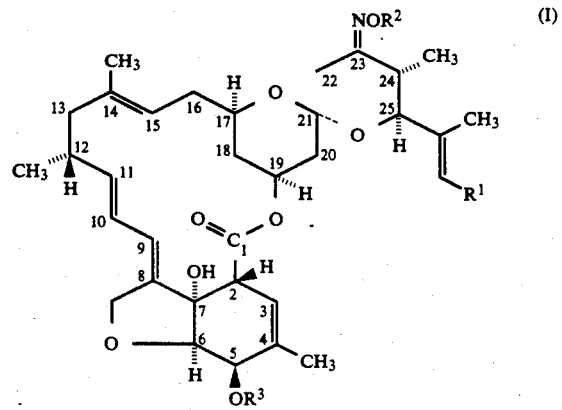

and salts thereof, wherein $R^1$ represents a methyl, ethyl or ispropyl group; $R^2$ represents a $C_{2-7}$ alkyl group interrupted by an oxygen or sulphur atom or an aryl, aryl $C_{1-7}$ alkyl or heteroaryl $C_{1-7}$ alkyl group; $OR^3$ is a hydroxyl group or a substituted hydroxyl group having up to 25 carbon atoms; and the group $=NOR^2$ is in the E configuration.

These compounds may be used for controlling insect, acarine, nematode or other pests.

8 Claims, No Drawings

MACROLIDE COMPOUNDS

"This is a continuation of co-pending application Ser. No. 07/242,184 filed on Sep. 9, 1988 now abandoned."

This invention relates to novel antibiotic compounds and to processes for their preparation.

United Kingdom Patent Specification No. 2166436A describes the production of Antibiotics S541 which may be isolated from the fermentation products of a novel Streptomyces sp.

We have now found a further group of compounds with antibiotic activity which may be prepared by chemical modification of Antibiotics S541. The novel compounds of the invention have antibiotic activity and/or are of use as intermediates in the preparation of other active compounds.

Thus, in one aspect, the invention particularly provides the compounds of formula (I)

and salts thereof, wherein $R^1$ represents a methyl, ethyl or isopropyl group; $R^2$ represents a $C_{2-7}$ alkyl group interrupted by an oxygen or sulphur atom or an aryl, $arylC_{1-7}alkyl$ or $heteroarylC_{1-7}alkyl$ group; $OR^3$ is a hydroxyl group or a substituted hydroxyl group having up to 25 carbon atoms; and the group $=NOR^2$ is in the E configuration.

The term 'aryl' as a group or part of a group in the compounds of formula (I) means phenyl optionally substituted by one or more nitro, halo, alkoxy or alkyl groups.

The heteroaryl portion of the heteroaryl $C_{1-7}$ alkyl group within the definition of $R^2$ is an unsaturated 5- or 6-membered monocyclic ring containing one or more heteroatoms selected from oxygen, nitrogen and sulphur.

When the compounds of formula (I) are to be used as intermediates $OR^3$ will often be a protected hydroxy group and the invention particularly includes such protected compounds.

When the group $OR^3$ in compounds of formula (I) is a substituted hydroxyl group it may represent an acyloxy group [e.g. a group of the formula $-OCOR^4$, $-OCO_2R^4$ or $-OCSOR^4$ (where $R^4$ is an aliphatic, araliphatic or aromatic group, for example an alkyl, alkenyl, alkynyl, cycloalkyl, aralkyl or aryl group)], a formyloxy group, a group $-OR^5$ (where $R^5$ is as defined above for $R^4$), a group $-OSO_2R^6$ (where $R^6$ is a $C_{1-4}$ alkyl or $C_{6-10}$ aryl group), a silyloxy group, a cyclic or acyclic acetaloxy group, a group $OCO(CH_2)_nCO_2R^7$ (where $R^7$ is a hydrogen atom or a group as defined for $R^4$ above and n represents zero, 1 or 2) or a group $OCONR^8R^9$ (where $R^8$ and $R^9$ may each independently represent a hydrogen atom or a $C_{1-4}$ alkyl group e.g. methyl).

Where $R^4$ or $R^5$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^4$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^5$ is a substituted alkyl group it may be substituted by a cycloalkyl e.g. cyclopropyl group.

Where $R^4$ or $R^5$ are alkenyl or alkynyl groups, they may be for example $C_{2-8}$ alkenyl, e.g. allyl, or $C_{2-8}$ alkynyl groups.

Where $R^4$ or $R^5$ are cycloalkyl groups, they may be for example $C_{3-12}$ cycloalkyl, such as $C_{3-7}$ cycloalkyl, e.g. cyclopentyl groups.

Where $R^4$ or $R^5$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include $phenC_{1-6}alkyl$, e.g. benzyl groups.

Where $R^4$ or $R^5$ are aryl groups, they may be carbocyclic or heterocyclic and preferably have 4–15 carbon atoms, and may be for example a phenyl group.

When $-OR^3$ is a group $-OSO_2R^6$, it may be for example a methylsulphonyloxy or p-toluenesulphonyloxy group.

Where $-OR^3$ represents a cyclic acetaloxy group, it may for example have 5–7 ring members and may be for example a tetrahydropyranyloxy group.

When $-OR^3$ represents a silyloxy group or $R^4$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^4$ and particularly include methyl, t-butyl and phenyl groups. Particular examples of such silyloxy groups are trimethylsilyloxy and t-butyldimethylsilyloxy.

Where $OR^3$ represents a group $OCO(CH_2)_nCO_2R^7$, it may for example be a group $OCOCO_2R^7$ or $OCOCH_2CH_2CO_2R^7$ where $R^7$ represents a hydrogen atom or a $C_{1-4}$ alkyl (e.g. methyl or ethyl) group.

Salts that may be formed with compounds of formula (I) containing an acidic group include salts with bases e.g. alkali metal salts such as sodium and potassium salts.

In the compounds of formula (I), the group $R^1$ is preferably an isopropyl group.

When $R^2$ in the compounds of formula (I) is a $C_{2-7}$ alkyl group interrupted by an oxygen or sulphur atom it may be for example a $C_{1-6}$ alkoxymethyl or $C_{1-6}$ alkylthiomethyl group, and is preferably methoxymethyl.

When $R^2$ is an aryl group, it may be for example phenyl.

When $R^2$ is an aryl $C_{1-7}$ alkyl group, it may be for example an arylmethyl group, and is preferably a benzyl or p-nitrobenzyl group.

When $R^2$ is a heteroaryl $C_{1-7}$ alkyl group, it may be for example a heteroarylmethyl group, and is preferably a pyridylmethyl, e.g. 4-pyridylmethyl group, or more preferably a 2-thienylmethyl group.

In the compounds of formula (I) the group $OR^3$ is preferably a methoxycarbonyloxy, or, especially, an acetoxy or hydroxy group. In general, compounds of formula (I) in which $OR^3$ is a hydroxy group are particularly preferred.

In the compounds of formula (I) $R^2$ is preferably methoxymethyl, benzyl, p-nitrobenzyl or thienylmethyl. Compounds of formula (I) in which $R^2$ is a p-nitrobenzyl group are particularly preferred.

Important compounds according to the invention are those of formula (I) in which $R^1$ is an isopropyl group, $R^2$ is a p-nitrobenzyl group and $OR^3$ is a hydroxy, acetoxy, or methoxycarbonyloxy group.

A particularly important active compound of the invention is that of formula (I) in which:

$R^1$ is an isopropyl group, $R^2$ is a p-nitrobenzyl group and $OR^3$ is a hydroxyl group;

As indicated previously, the compounds according to the invention may be of use as antibiotics and/or as intermediates for the preparation of other active compounds. When the compounds of the invention are to be used as intermediates, the $-OR^3$ group may be a protected hydroxyl group. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, New York 1981) and "Protective Groups in Organic Chemistry" by J F W McOmie (Plenum Press, London, 1973). Examples of $OR^3$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans*. In particular, we have found that compounds of the invention are active in vivo against parasitic nematodes such as *Nematospiroides dubius*.

Compounds of the invention are also of use as antifungals, for example, against strains of *Candida* sp. such as *Candida albicans* and *Candida glabrata* and against yeast such as *Saccharomyces carlsbergensis*.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae*, *Aulacorthum circumflexum*, *Myzus persicae*, *Nephotettix cincticeps*, *Nilparvata lugens*, *Panonychus ulmi*, *Phorodon humuli*, *Phyllocoptruta oleivora*, *Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); filler (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be includeed.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically aceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 $\mu$g/kg bodyweight, preferably from 50–1000 $\mu$g/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates; powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the invention may be prepared by the processes discussed below. In some of these processes it may be necessary to protect a hydroxyl group at the 5-position in the starting material prior to effecting the reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

Thus, for example, an acyl group such as an acetyl group may be removed by basic hydrolysis e.g. using sodium or potassium hydroxide in aqueous alcohol. Acetal groups such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the presence of a thiol (e.g. ethanethiol) in a suitable solvent such as dichloromethane at e.g. room temperature.

According to one aspect of the invention we provide a process for the preparation of compounds of formula (I) which comprises reacting compounds of formula (II):

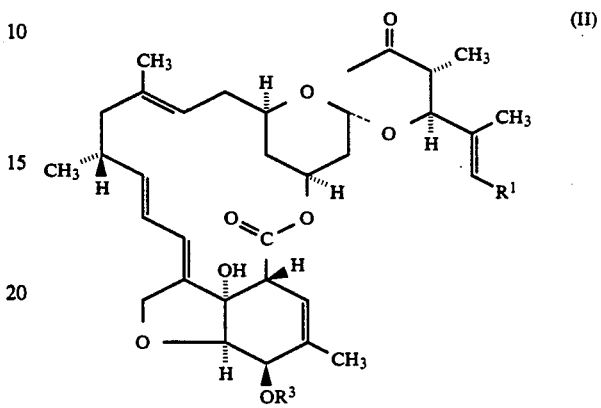

(where $R^1$ and $OR^3$ are as previously defined) with a reagent $H_2NOR^2$ (where $R^2$ is as previously defined), and if desired followed by deprotection of a compound of formula (I) in which $OR^3$ is a protected hydroxyl group.

The reaction may be conveniently carried out at a temperature in the range $-20°$ to $+100°$ C., e.g. $-10°$ to $+50°$ C. in a suitable solvent. It is convenient to use the reagent $H_2NOR^2$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic ethers such as tetrahydrofuran or dioxan, and acylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a co-solvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

According to a further aspect of the invention we provide a further process for the preparation of compounds of formula (I) in which $OR^3$ is a substituted hydroxyl group which comprises reacting a compound of formula (I) in which $OR^3$ is a hydroxyl group with a reagent serving to convert a hydroxyl group into a substituted hydroxyl group.

The reaction will in general be an acylation, formylation, sulphonylation, etherification, silylation or acetal formation.

Thus, for example, acylation may be effected using an acylating agent such as an acid of formula $R^4COOH$ or a reactive derivative thereof, such as an acid halide (e.g. acid chloride), anhydride or activated ester, or a reactive derivative of a carbonic acid $R^4OCOOH$ or thiocarbonic acid $R^4OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^6SO_3H$ such as a sulphonyl halide, for example a chloride $R^6SO_2Cl$ or a sulphonic anhydride. The sulphonylation is preferably effected in the presence of a suitable acid binding agent as described above.

Etherification may be effected using a reagent of formula $R^5Y$ (where $R^5$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be carried out by formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^5Y$.

Alternatively, the reaction may be effected in the presence of a silver salt such as silver oxide, silver perchlorate, silver carbonate or silver salicylate or mixtures thereof, and this system may be particularly appropriate when etherification is carried out using an alkyl halide (e.g. methyl iodide).

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Solvents which may be employed in the above reactions include ketones (e.g. acetone), amides (e.g. N,N-dimethylformamide, N,N-dimethylacetamide or hexamethylphosporamide), ethers (e.g. cyclic ethers such as tetrahydrofuran or dioxan, and acyclic ethers such as dimethoxyethane or diethylether), nitriles (e.g. acetonitrile), hydrocarbons such as halogenated hydrocarbons (e.g. methylene chloride), and esters such as ethyl acetate, as well as mixtures of two or more such solvents.

Silylation may be effected by reaction with a silyl halide (e.g. chloride), advantageously in the presence of a base such as imidazole triethylamine or pyridine, using a solvent such as dimethylformamide.

According to another aspect of the invention we provide a further process for the preparation of compounds of formula (I) which comprises reacting a compound of formula (I) in which $R^2$ is a hydrogen atom and $OR^3$ is a substituted hydroxyl group with an alkylating agent $R^2Y$ (where $R^2$ is as defined in formula (I) and Y is as previously defined), and if desired followed by deprotection of a compound of formula (I) in which $OR^3$ is a protected hydroxyl group.

The etherification reaction may be carried out by formation of a magnesium alkoxide using a Grignard reagent such as a methylmagnesium halide e.g. methylmagnesium iodide or using a trialkylsilymethylmagnesium halide e.g. trimethylsilylmethylmagnesium chloride followed by treatment with the reagent $R^2Y$. The reaction may conveniently be effected at room temperature in the presence of a solvent such as an amide e.g. hexamethylphosphoric triamide.

Compounds of formula (I) in which $R^2$ is a hydrogen atom and $OR^3$ is a substituted hydroxyl group may be prepared from a suitable compound of formula (II) by reaction with hydroxylamine hydrochloride according to the general method described above for the preparation of compounds of formula (I) from compounds of formula (II).

Compounds of formula (II) may be prepared by oxidising a compound of formula (III)

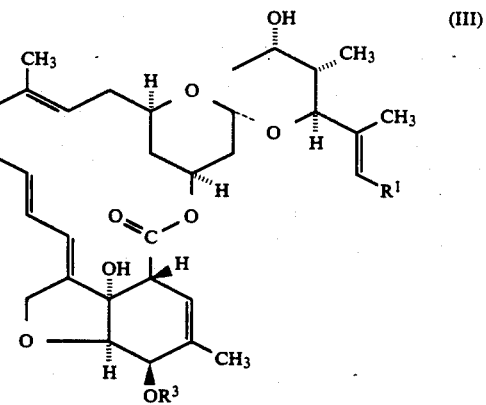

wherein $R^1$ is as defined previously and $OR^3$ is a substituted hydroxyl group, and if desired followed by deprotection of a compound of formula (II) in which $OR^3$ is a protected hydroxyl group.

The reaction may be effected with an oxidising agent serving to convert a secondary hydroxyl group to an oxo group, whereby a compound of formula (II) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl chloride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used. The choice of solvent will depend upon the type of oxidising agent used for the conversion.

The reaction may be carried out at a temperature of from $-80°$ C. to $+50°$ C.

Salts of acids of formula (I) may be prepared by conventional methods, for example by treating the acid with a base or converting one salt into another by exchange of ion.

The intermediate Antibiotics S541 compounds of formula (III) in which $OR^3$ is a hydroxy or methoxy group may be obtained using the fermentation and isolation methods described in UK Patent Specification No. 2166436A. Other intermediates of formula (III) may be prepared from these compounds using the methods described above for the preparation of compounds of formula (I) in which $OR^3$ is a substituted hydroxyl group from corresponding compounds in which $OR^3$ is a hydroxyl group.

The intermediate Antibiotics S541 compound of formula (III) in which $R^1$ is an isopropyl group and $OR^3$ is hydroxy is hereinafter referred to as 'Factor A'.

The following Preparations and Examples illustrate the invention. All temperatures are in °C.

PREPARATION 1

5-Acetoxy Factor A

Factor A (3.0 g) in pyridine (20 ml) at $-5°$ was treated with acetic anhydride (8 ml) and the resulting solution left at 3° for 20 hr. Benzene (100 ml) was added and the solution concentrated in vacuo. The residual oil was chromatographed over silica using dichloromethane:acetone (40:1) as eluent to give 5-acetoxy Factor A (2.06 g), containing 10% 5,23-diacetoxy Factor A. The compounds were separated by reverse-phase preparative hplc to give the title compound (79% recovery), $\lambda_{max}$ (EtOH) 244.5 nm ($E_1^1$ 462), $\delta$ (CDCl$_3$) includes 2.14 (s; 3H), m/z includes 654, 594 and 576.

PREPARATION 2

5-Acetoxy-23-keto Factor A

A solution of oxalyl chloride (1.96 ml) in dry dichloromethane (25 ml) at $-70°$ under nitrogen was treated dropwise with a solution of dimethylsulphoxide (3.19 ml) in dry dichloromethane (15 ml) and then dropwise with a solution of the product of Preparation 1 (4.91 g) in dry dichloromethane (30 ml). The resulting solution was stirred at $-70°$ for 1.5 hr before being treated dropwise with a solution of triethylamine (12.6 ml) in dry dichloromethane (40 ml). The reaction mixture was stirred for 1.25 hr without cooling and poured into a mixture of cold water (500 ml) and ether (500 ml). The aqueous layer was extracted with ether (2×200 ml). The combined organic layers were washed with water (4×200 ml), brine (500 ml), dried and evaporated. The residual foam was chromatographed over silica using dichloromethane: acetone (50:1) to give the title compound (3.4 g) $\delta$ (CDCl$_3$) include 3.33 (m; 1H), 3.49 (m; 1H), 3.70 (d10; 1H) and 5.52 (d5; 1H), m/z include 652, 634, 609, 591, 574, 482, 263, 235 and 151.

PREPARATION 3

23-Keto Factor A

The production of Preparation 2 (276 mg) in methanol (5 ml) at 0° was treated dropwise with a solution of N-sodium hydroxide (0.42 ml) in methanol (1.0 ml). The solution was left at 5° for 5 hr before being poured into cold water. The mixture was extracted with ether and ethyl acetate. The combined organic layers were washed with brine, dried, and evaporated to leave a solid, which was purified by preparative tlc using dichloromethane:acetone (10:1) as solvent to give the title compound (140 mg), $\delta$ (CDCl$_3$) include 3.28 (m; 1H), 3.48 (m; 1H), 3.70 (d10; 1H) and 4.28 (tr7; 1H), m/z include 592, 549, 482, 370, 263, 235 and 151.

PREPARATION 4

5-Acetoxy-23[E]-hydroxyimino Factor A

The title compound was prepared by reacting the product of Preparation 2 with hydroxylamine hydrochloride according to the method described in Example 1 below. The crude product was purified by chromatography over Merck Kieselgel 60 230–400 mesh, eluting with ethyl acetate:acetonitrile (4:1) to afford the title compound as a colourless foam. $\delta$r99Cl$_3$) includes 8.12 (s; 1H), 5.5–5.6(m:2H), 3.42 (d15; 1H), 2.16 (s; 3H).

EXAMPLE 1

23[E]-Benzyloxyimino Factor A

Sodium acetate (151 mg) and benzyloxyamine hydrochloride (306 mg) were added to a soultion of the product of Preparation 3 (203 mg) in method (20 ml). The solution was stirred at 20° for 3 h, concentrated to Ca 7 ml and after dilution with ethyl acetate (40 ml), was successively washed with 0.5N hydrochloric acid and water. The dried organic phase was evaporated to afford an off-white foam (228 mg) which was purified by chromatography over Merck Keiselgel 60 230–400 ml (80 ml). Elution of the column with hexane:acetate (3:2) afforded the title compound as a white foam. $[\alpha]_D^{21} +119°$, (c 1.21, CHCl$_3$); $\lambda_{max}$ (EtOH) 244 nm ($\epsilon$29,500); $_{max}$ (CHBr$_3$) 3540, 3450 (OH), 1704 (C=O), and 990 cm$^{-1}$ (C—O); $\delta$ (CDCl$_3$) include 7.2–7.4 (m; 5H), 5.12(s; 2H), 4.29(t6; 1H), 3.96(d; 1H), 3.41(d14; 1H), 0.99(d6; 3H), 0.96(d6; 3H), 0.89(d6; 3H).

The products of Examples 2–5 were prepared in a similar manner from the product of Preparation 3 and the appropriate oxime hydrochloride.

EXAMPLE 2

23[E]-4-Pyridylmethoxyimino Factor A

4-Pyridylmethoxyamine hydrochloride gave the title compound as a white foam. $[\alpha]_D^{21} +106°$ (c 0.93, CHCl$_3$); $\lambda_{max}$ (EtOH) 244 nm ($\epsilon$30,400); $_{max}$ (CHBr$_3$)

3540, 3460 (OH) 1710 (C=O) and 994 cm$^{-1}$(C—O)-; δ (CDCl$_3$) include 8.52 (d 6; 2H), 7.25 (d 6; 2H), 5.20, 5.11 (AB q 15; 2H), 4.30 (d 6; 1H), 3.96 (d6;1H), 3.47 (d 14; 1H), 1.00(d6; 3H), 0.96(d 6; 3H), 0.84(d6; 3H).

EXAMPLE 3

23[E]-2-Thienylmethoxyimino Factor A

Thienylmethoxyamine hydrochloride gave the title compound as a white foam. $[\alpha]_D^{21}+121°$ (c 1.36, CHCl$_3$); $\lambda_{max}$ (EtOH) 245 nm (ε34,900); $_{max}$ (CHBr$_3$) 3540, 3460 (OH), 1708 (C=O), and 992 cm$^{-1}$ (C—O); δ(CDCl$_3$) include 7.26 (d5; 1H), 7.03(d3; 1H), 6.96(dd 3; H), 5.21(s; 2H), 4.28(t7; 1H), 3.96(d 6; 1H), 3.30 (d 14; 1H), 0.99(d6; 3H), 0.96 (d6; 3H), 0.94(d6; 3H).

EXAMPLE 4

23[E]-4-Nitrobenzyloxyimino Factor A

4-Nitrobenzyloxyamine hydrochloride gave the title compound as a white foam. $[\alpha]_D^{21}+89°$, (c 0.99, CHCl$_3$); $\lambda_{max}$ (EtOH) 245 nm (ε34,600); $_{max}$ (CHBr$_3$) 3460, (OH), 1708 (C=O), 1518, 1340 (NO$_2$), 990 (C—O);δ include 8.18 (d9; 2H), 7.48(d9; 2H), 5.1–5.3(m; 3H), 4.30 (t6; 1H), 3.46 (d14; 1H).

EXAMPLE 5

23[E]-Phenoxyimino Factor A

Phenoxyamine hydrochloride gave the title compound as a white foam. $[\alpha]_D^{21}+67°$ (c 0.86, CHCl$_3$); $\lambda_{max}$ (EtOH) 237 nm (ε 42,100); $_{max}$ (CHBr$_3$) (cm$^{-1}$) 3540, 3460 (OH), 1708 (C=O), and 990 (C—O); δ (CDCl$_3$) include 6.9–7.4 (m; 5H) 5.44 (s; 1H), 4.30 (t6; 1H),3.54 (d15; 1H), 1.89 (s; 3H), 0.9–1.1 (m; 12H).

EXAMPLE 6

5-Acetoxy 23[E]-methoxymethoxyimino Factor A

A 3-molar solution of methylmagnesium iodide (0.3 ml) was added to a stirred solution of 5-acetoxy-23[E]-hydroxyimino Factor A (328 mg) in dry hexamethylphosphoric triamide (10 ml) under nitrogen. After 5 min, bromomethyl methyl ether (0.065 ml) was added and, after a further 20 min, ether (40 ml) and 0.5N hydrochloric acid (50 ml) were added. The organic phase was washed successively with 0.5N hydrochloric acid, water, and brine and the dried organic phase was evaporated. The crude product was purified by chromatography over Meck kieselgel 60 230–400 mesh (80 ml). Elution of the column with hexane: ethyl acetate (2:1) afforded the title compound as a white foam. $[\alpha]_D^{21}+134°$ (c 1.22, CHCl$_3$); $\lambda_{max}$ (EtOH) 244 nm (ε 28.100); $\nu_{max}$ (CHBr$_3$) (cm$^{-1}$) 3450 (OH) 1730 (OAc), 1710 (C=O), 1010, 992 (C—O); δ (CDCl$_3$) include 5.56 (M; 2H), 5.10+5.14 (ABq 8; 2H), 3.42 (s; 3H), 3.38(d 14; 1H), 2.18 (s; 3H).

EXAMPLE 7

23[E]-Methoxymethoxyimino Factor A

A solution containing 5-acetoxy-23[E]-methoxymethoxyimino Factor A (75 mg) and 1N sodium hydroxide (0.5 ml) in methanol (10 ml) was stirred in an ice bath for 1.5 h. After diluting with ethyl acetate (40 ml) the mixture was washed successively with 0.5N hydrochloric acid and water. The dried organic phase was evaporated and the resultant white solid was purified by chromatography over Merck Kieselgel 60 230–400 mesh. Elution of the column with hexane: ethyl acetate (2:1) afforded the title compound as a white foam. $[\alpha]_D^{21}+135°$ (c 1.12, CHCl$_3$); $\lambda_{max}$ (EtOH) 244 nm (ε 27,100); $\nu_{max}$ (cm$^{-1}$) (CHBr$_3$) 3540, 3480 (OH), 1708 (C=O), 1010, 992 (C—O); δ (CDCl$_3$) include 5.41 (s; 1H), 5.10 (s; 2H), 3.40 (s; 3H), 3.36 (d 14; 1H).

EXAMPLE 8

23-[E]-4-Nitrobenzyloxyimino Factor A

A solution containing 23-keto Factor A (237 mg) sodium acetate (190 mg) and 4-nitrobenzyloxyamine hydrochloride (187 mg) in methanol (40 ml) was stirred at 20° for 24 h. after which time more 4-nitrobenzyloxyamine hydrochloride (110 mg) was added. The solution was kept at 20° for 3 days, then concentrated to ca 5 ml, diluted with ethyl acetate (50 ml) and washed successively with 0.5N hydrochloric acid, water and brine. The dried organic phase was evaporated and the crude product was purified by chromatography over Merck Kieselgel 60 230–400 mesh (150 ml). Elution of the column with hexane:ethyl acetate (2:1) afforded the title compound as a white foam (73%) $[\alpha]_D^{21}+89°$ (c 0.99, CHCl$_3$), $\lambda_{max}$ (EtOH) 245 nm (ε 34,600) $\nu_{max}$ (CHBr$_3$) (cm$^{-1}$) 3540, 3460 (OH) 1708 (C=O), 1518, 1340 (NO$_2$), 990 (C—O), δ (CDCl$_3$) include 8.18 (d9; 2H), 7.48 (d9; 2H), 5.1–5.3 (m; 3H), 4.30 (t6; 1H) 3.46 (d14; 1H).

The following are examples of formulations according to the invention. The term 'Active Ingredient' as used hereinafter means a compound of the invention.

MULTIDOSE PARENTERAL INJECTION

Example 1

|  | % w/v | Range |
|---|---|---|
| Active ingredient | 2.0 | 0.1–6.0% w/v |
| Benzyl alcohol | 1.0 |  |
| Polysorbate 80 | 10.0 |  |
| Glycerol formal | 50.0 |  |
| Water for Injections | to 100.0 |  |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

Example 2

|  | % w/v | Range |
|---|---|---|
| Active ingredient | 4.0 | 0.1–7.5% w/v |
| Benzyl alcohol | 2.0 |  |
| Glyceryl triacetate | 30.0 |  |
| Propylene glycol | to 100.0 |  |

Dissolve the active ingredient in the benzyl alcohol and glyceryl triacetate. Add the propylene glycol and make up to volume. Sterilize the product by conventional pharmaceutical methods, for example sterile filtration, and package aseptically.

Example 3

|  | % | Range |
|---|---|---|
| Active ingredient | 2.0 w/v | 0.1–7.5% w/v |
| Ethanol | 36.0 v/v |  |
| Non-ionic surfactant | 10.0 w/v |  |
| (e.g. Synperonic PE L44*) |  |  |

-continued

|  | % | Range |
|---|---|---|
| Propylene glycol | to 100.0 | |

*Trademark of ICI

Dissolve the active ingredient in the ethanol and surfactant and make up to volume. Sterilize the product by conventional pharmaceutical methods, for example sterile filtration, and package aseptically.

Example 4

|  | % | Range |
|---|---|---|
| Active Ingredient | 2.0 w/v | 0.1–3.0% w/v |
| Non-ionic surfactant (e.g. Synperonic PE F68*) | 2.0 w/v | |
| Benzyl alcohol | 1.0 w/v | |
| Miglyol 840** | 16.0 v/v | |
| Water for Injections | to 100.0 | |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

Aerosol spray

|  | % w/w | Range |
|---|---|---|
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dustcaps.

Tablet

Method of manufacture—wet granulation

|  | mg |
|---|---|
| Active Ingredient | 250.0 |
| Magnesium stearate | 4.5 |
| Maize starch | 22.5 |
| Sodium starch glycolate | 9.0 |
| Sodium lauryl sulphate | 4.5 |

Microcrystalline cellulose to tablet core weight of 450 mg Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

Veterinary tablet for small/domestic animal use

Method of manufacture—dry granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

Veterinary intrammary injection

|  |  | mg/dose | Range |
|---|---|---|---|
| Active Ingredient | | 150 mg | 0.05–1.0 g |
| Polysorbate 60 | 3.0% w/w | to 3 g | to 3 or 15 g |
| White Beeswax | 6.0% w/w | | |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

Veterinary slow-release bolus

|  | % w/w | Range |
|---|---|---|
| Active Ingredient | | 0.25–2 g |
| Colloidal silicon dioxide | 2.0 | to required fill weight |
| Microcrystalline cellulose | to 100.0 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

Veterinary oral drench

|  | % w/v | Range |
|---|---|---|
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

Veterinary oral paste

|  | % w/w | Range |
|---|---|---|
| Active Ingredient | 4.0 | 1-20% w/w |
| Saccharin sodium | 2.5 | |
| Polysorbate 85 | 3.0 | |
| Aluminium distearate | 5.0 | |
| Fractionated coconut oil | to 100.0 | |

Disperse the aluminium distearate in the fractionated coconut oil and polysorbate 85 by heating. Cool to room temperature and disperse the saccharin sodium in the oily vehicle. Disperse the active ingredient in the base. Fill into plastic syringes.

Granules for veterinary in-feed administration

|  | % w/w | Range |
|---|---|---|
| Active Ingredient | 2.5 | 0.05-5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

Veterinary Pour-on

|  | % w/v | Range |
|---|---|---|
| Active Ingredient | 2.0 | 0.1 to 30% |
| Dimethyl sulphoxide | 10.0 | |
| Methyl Isobutyl ketone | 30.0 | |
| Propylene glycol (and pigment) | to 100.0 | |

Dissolve the active ingredient in the dimethyl sulphoxide and the methyl isobutyl ketone. Add the pigment and make up to volume with the propylene glycol. Fill into the pour-on container.

Emulsifiable Concentrate

| Active ingredient | 50 g |
|---|---|
| Anionic emulsifier (e.g. Phenyl sulphonate CALX) | 40 g |
| Non-ionic emulsifier (e.g. Synperonic NP13)* | 60 g |
| Aromatic solvent e.g. Solvesso 100) to 1 liter. | |

*Trademark of ICI

Mix all ingredients, stir until dissolved.

Granules

| (a) | Active ingredient | 50 g |
|---|---|---|
| | Wood resin | 40 g |
| | Gypsum granules (20-60 mesh) to 1 kg (e.g. Agsorb 100A) | |
| (b) | Active ingredient | 50 g |
| | Synperonic NP13* | 40 g |
| | Gypsum granules (20-60 mesh) to 1 kg. | |

*Trademark of ICI

Dissolve all ingredients in a volatile solvent e.g. methylene chloride, add to granules tumbling in mixer. Dry to remove solvent.

We claim:
1. A compound of formula (I)

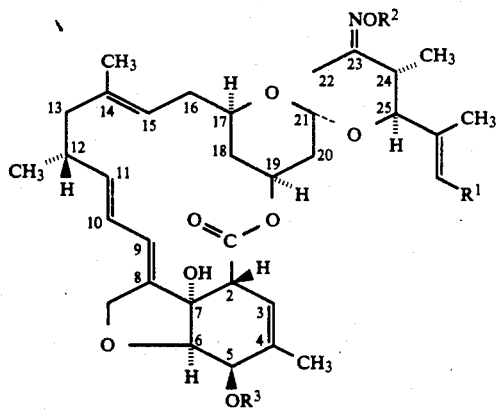

or a pharmaceutically or an agronomically acceptable salt thereof, wherein $R^1$ represents a methyl, ethyl or isopropyl group; $R^2$ represents a $C_5$-$C_7$ alkyl group interrupted by an oxygen, $C_2$-$C_7$ alkyl group interrupted by a sulphur atom, phenyl $C_2$-$C_7$ alkyl optionally substituted by nitrogen, halogen, $C_1$-$C_7$ alkoxy or $C_1$-$C_7$ alkyl or $C_1$-$C_7$ alkyl group substituted with an unsaturated 5-membered monocyclic ring containing one heteroatom selected from the group consisting of oxygen, nitrogen and sulphur or an unsaturated 6-membered monocyclic ring containing one nitrogen; $OR^3$ is a hydroxyl group, $OCOR^4$, $OCO_2R^4$, $OCSOR^4$, formyloxy group, $OR^5$, $OSO_2R^6$, a silyloxy group, a cyclic or acyclic acetaloxy group, $OCO(CH_2)_nCO_2R^7$, where n represents zero, 1 or 2, or $OCONR^8R^9$; wherein $R^4$ and $R^5$ are each independently $C_1$-$C_8$ alkyl, $C_2$-$C_8$ alkenyl, $C_2$-$C_8$ alkynyl, $C_3$-$C_{12}$ cycloalkyl, phenyl, an unsaturated 5-membered monocyclic ring containing one heteroatom selected from the group consisting of oxygen, nitrogen and sulphur, an unsaturated 6-membered monocyclic ring containing one nitrogen or $C_1$-$C_6$ alkyl group substituted with a phenyl, an unsaturated 5-membered monocyclic ring containing one heteroatom selected from the group consisting of oxygen, nitrogen and sulphur or an unsaturated 6-membered monocyclic ring containing one nitrogen; $R^6$ is a $C_1$-$C_4$ alkyl, phenyl or naphthyl; $R^7$ is a hydrogen atom, $C_1$-$C_8$ alkyl, $C_2$-$C_8$ alkenyl, $C_2$-$C_8$ alkynyl, $C_3$-$C_{12}$ cycloalkyl, phenyl, an unsaturated 5-membered monocyclic ring containing one heteroatom selected from the group consisting of oxygen, nitrogen and sulphur, an unsaturated 6-membered monocyclic ring containing one nitrogen or $C_1$-$C_6$ alkyl group substituted with a phenyl, an unsaturated 5-membered monocyclic ring containing one heteroatom selected from the group consisting of oxygen, nitrogen and sulphur or an unsaturated 6-membered monocyclic ring containing one nitrogen; and $R^8$ and $R^9$ are each independently a hydrogen atom or $C_1$-$C_4$ alkyl; and the group $=NOR^2$ is in the E configuration.

2. The compound according to claim 1 in which $R^1$ is an isopropyl group.

3. The compound according to claim 1 or claim 2 in which $R^2$ is a p-nitrobenzyl or thienylmethyl group.

4. The compound according to any preceding claim in which $OR^3$ is a methoxycarbonyloxy, acetoxy or hydroxy group.

5. The compound according to claim 1 in which $R^1$ is an isopropyl group, $R^2$ is a p-nitrobenzyl group and $OR^3$ is a hydroxy group.

6. A composition for parenteral, oral, rectal, topical, implant, ophthalmic, nasal or genito-urinary use in human or veterinary medicine comprising a pharmaceutically effective amount of a compound according to claim 1 together with one or more carriers or excipients.

7. A pest control composition comprising a pesticidally effective amount of a compound according to claim 1 together with one or more carriers or excipients.

8. A method for combatting pests in a location of the pests, which comprises applying to plants, the pests themselves or the location thereof an effective amount of a compound according to claim 1.

* * * * *

UNITED STATES PATENT AND TRADEMARK OFFICE
CERTIFICATE OF CORRECTION

PATENT NO. : 5,192,777
DATED : March 9, 1993
INVENTOR(S) : Michael V. J. Ramsay, et al It is certified that error appears in the above-indentified patent and that said Letters Patent is hereby corrected as shown below:

In the Abstract, Formula (I):

Column 1

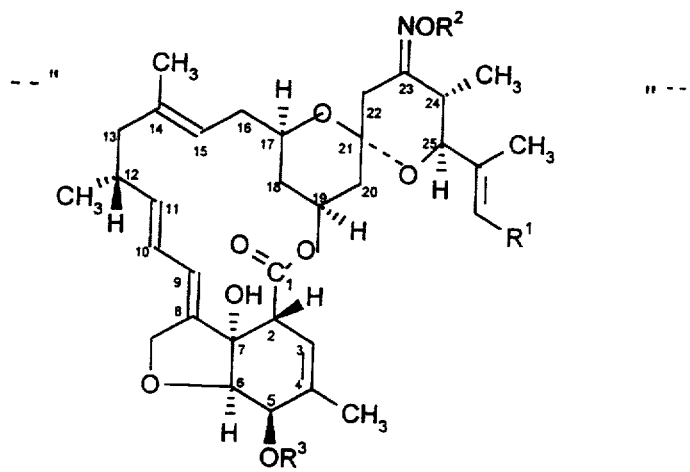

UNITED STATES PATENT AND TRADEMARK OFFICE
CERTIFICATE OF CORRECTION

PATENT NO. : 5,192,777
DATED : March 9, 1993
INVENTOR(S) : Michael V.J. Ramsay, et al It is certified that error appears in the above-indentified patent and that said Letters Patent is hereby corrected as shown below:

In Column 8, Formula (II)

-- " 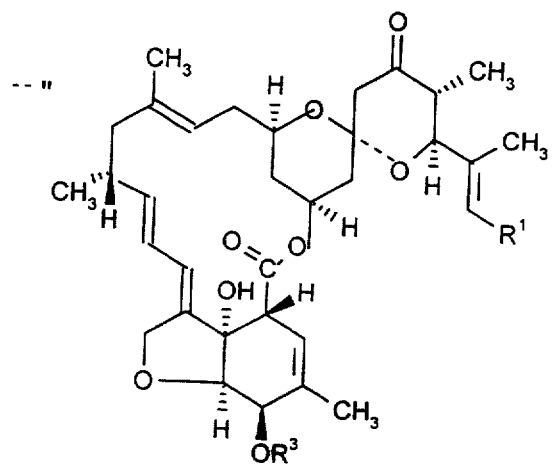 " --

UNITED STATES PATENT AND TRADEMARK OFFICE
CERTIFICATE OF CORRECTION

PATENT NO. : 5,192,777

DATED : March 9, 1993

INVENTOR(S) : Michael V.J. Ramsay, et al.

It is certified that error appears in the above-identified patent and that said Letters Patent is hereby corrected as shown below:

In Column 10, Formula (III)

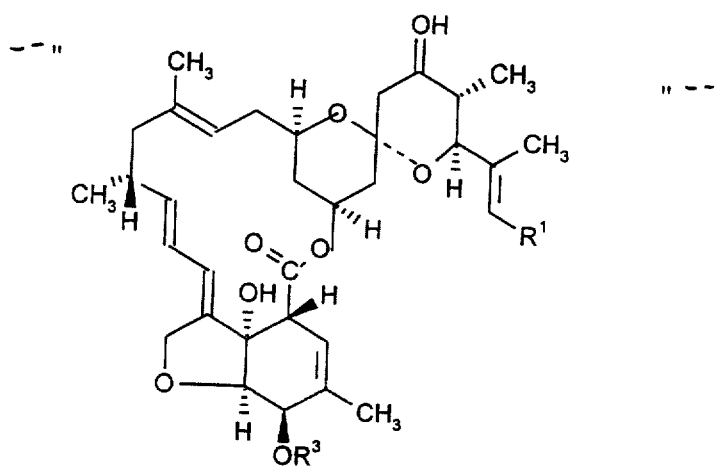

UNITED STATES PATENT AND TRADEMARK OFFICE
CERTIFICATE OF CORRECTION

PATENT NO. : 5,192,777
DATED : March 9, 1993
INVENTOR(S) : Michael V.J. Ramsay, et al It is certified that error appears in the above-indentified patent and that said Letters Patent is hereby corrected as shown below:

Claim 1, Column 18, Formula (I)

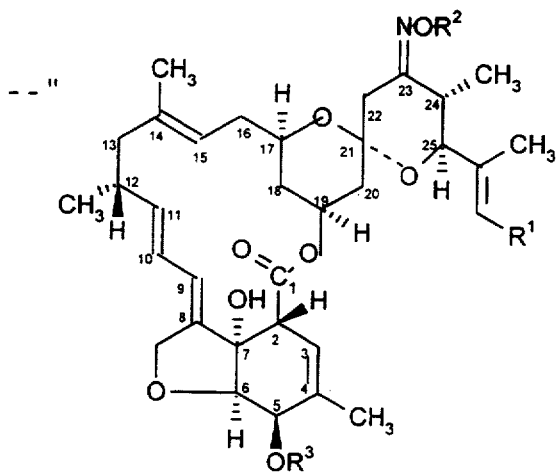

Signed and Sealed this

Fourth Day of February, 1997

Attest:

BRUCE LEHMAN

Attesting Officer

Commissioner of Patents and Trademarks